United States Patent
Xu et al.

(10) Patent No.: US 10,732,109 B2
(45) Date of Patent: Aug. 4, 2020

(54) CORE-SHELL TYPE NANOSILICA FLUORESCENT PROBE AND SYNTHESIS METHOD AND USE THEREOF

(71) Applicants: Guangdong Institute of Microbiology (Guangdong Detection Center of Microbiology), Guangzhou (CN); GUANGDONG ACADEMY OF SCIENCES, Guangzhou (CN)

(72) Inventors: Meiying Xu, Guangzhou (CN); Fei Liu, Guangzhou (CN); Bing Liao, Guangzhou (CN); Yeshen Luo, Guangzhou (CN); Enze Li, Guangzhou (CN)

(73) Assignee: Guangdong Institute of Microbiology (Guangdong Detection Center of Microbiology), Guangzhou (CN)

( * ) Notice: Subject to any disclaimer, the term of this patent is extended or adjusted under 35 U.S.C. 154(b) by 0 days.

(21) Appl. No.: 16/492,161

(22) PCT Filed: Sep. 26, 2018

(86) PCT No.: PCT/CN2018/107590
§ 371 (c)(1),
(2) Date: Sep. 9, 2019

(87) PCT Pub. No.: WO2019/105123
PCT Pub. Date: Jun. 6, 2019

(65) Prior Publication Data
US 2020/0080938 A1    Mar. 12, 2020

(30) Foreign Application Priority Data

Nov. 28, 2017 (CN) .......................... 2017 1 1215404

(51) Int. Cl.
*G01N 21/64* (2006.01)
*G01N 33/569* (2006.01)
*C09K 11/06* (2006.01)
*C09B 67/02* (2006.01)
*C09B 11/24* (2006.01)
*C09B 29/08* (2006.01)

(52) U.S. Cl.
CPC .......... *G01N 21/6428* (2013.01); *C09B 11/24* (2013.01); *C09B 29/08* (2013.01); *C09B 67/0097* (2013.01); *C09K 11/06* (2013.01); *G01N 33/56911* (2013.01); *G01N 2021/6439* (2013.01)

(58) Field of Classification Search
CPC ......... G01N 21/6428; G01N 33/56911; G01N 2021/6439; C09B 11/24; C09B 29/08; C09B 67/0097; C09K 11/06
USPC .......................................... 534/551
See application file for complete search history.

(56) References Cited

FOREIGN PATENT DOCUMENTS

| CN | 102830101 A | 12/2012 | |
|---|---|---|---|
| CN | 104830311 A | 8/2015 | |
| CN | 104843862 A | 8/2015 | |
| CN | 105417728 A | 3/2016 | |
| CN | 105920620 A | 9/2016 | |
| CN | 108003862 A | 5/2018 | |
| WO | 2011042564 A1 | 4/2011 | |
| WO | WO-2011042564 A1 * | 4/2011 | .......... G01N 33/552 |

\* cited by examiner

*Primary Examiner* — Kristin A Vajda
(74) *Attorney, Agent, or Firm* — Bayramoglu Law Offices LLC (57) ABSTRACT

Disclosed are a core-shell type nanosilica fluorescent probe and a synthesis method thereof, wherein the core-shell type nanosilica fluorescent probe is a nanoparticle with a core-shell structure. Also disclosed is a method using the core-shell type nanosilica fluorescent probe for selection of functional microorganisms having toxic aromatic hydrocarbon degrading activity, wherein the method enables efficient, intuitive and rapid specificity sorting and analyzing of individual cells with high sensitively.

5 Claims, 8 Drawing Sheets

CORE-SHELL TYPE NANOSILICA FLUORESCENT PROBE AND SYNTHESIS METHOD AND USE THEREOF

CROSS REFERENCE TO RELATED APPLICATIONS

This application is the national phase entry of International Application No. PCT/CN2018/107590, filed on Sep. 26, 2018, which is based upon and claims priority to Chinese Patent Application No. 201711215404.2, filed on Nov. 28, 2017, the entire contents of which are incorporated herein by reference.

TECHNICAL FIELD

The present invention relates to the technical field of selection of functional microorganism, and in particularly, the present invention relates to a core-shell type nanosilica fluorescent probe, a synthesis method thereof, and use thereof in selection of functional microorganisms.

BACKGROUND

With the rapid development of modern industry, the production and variety of synthetic aromatic hydrocarbon compounds are increasing. These compounds are complex in structure and difficult to degrade naturally, exhibit carcinogenic or teratogenic activity to humans, can be transported over long distances in media such as the atmosphere, water, soil and organisms, causing widespread nonpoint source pollution and seriously threatening human health and ecological security. Thus, pollution control of aromatic hydrocarbon compounds is a major problem in ecological environmental protection.

Microorganisms are important drivers of material cycle and energy conversion in ecosystem, having the ability to degrade pollutants into non-toxic and harmless products. Using microorganisms to purify toxic and hazardous substances has been considered to be the most promising means of environmental pollution control at present. For a long period, scientists have carried out research on microbial degradation of organic pollutants from different angles. With the development and application of analysis and detection technology based on microbial physiology and ecology, a large number of studies have shown that, functional microorganisms that can degrade toxic aromatic hydrocarbon pollutants using their own enzyme systems are widely found in polluted environments. These microorganisms with degradation function play an irreplaceable role in the purification and recovery of polluted environment, and are an important force for accelerating the removal of aromatic hydrocarbon pollutants.

The isolation and selection of microorganisms capable of efficiently degrading aromatic hydrocarbon pollutants is the core task for the control and recovery of aromatic hydrocarbon-polluted environment and accelerating the removal of aromatic hydrocarbon pollutants. For a single cell obtained by the conventional plate isolation and screening techniques, its characteristics and function will be manifested only after this single clone proliferates to form a population, which results in delay and low sensitivity in function characterization. Meanwhile, the heterogeneity between microbial cells in a population will lead to uncertainty in the function characterization, which reduces the accuracy of screening. Moreover, the conventional screening methods are only applicable for selecting the functional microorganisms that grow faster in specific media, but inapplicable for the analysis and selection of microorganisms that are difficult to grow or grow slowly. Thus, rapid and accurate analysis and screening of microbial functional activity at single cell level is the key to efficient selection of functional microorganisms.

Compared with the traditional analysis and detection techniques for cell function and metabolic activity, such as enzyme activity detection and metabolite analysis, fluorescent labeling technique is a rapid and convenient biological analysis method. Fluorescence-activated cell sorting (flow cytometry) enables rapid, high-sensitivity analytical sorting of single cells. However, fluorescent probes used in bacteria screening studies are mostly generic nucleic acid probes, which is inapplicable for tracking the functional activity of microorganisms. Nanoscale fluorescent probes used for tracking microorganisms, as they exhibit high locating capability and the fluorescent substances will not be easily leaked, can solve the problem of non-specific tracking of microbial functional cells. Using fluorescence energy transfer technology to construct nanoscale fluorescent probes for target contaminants, which realizes rapid, accurate analysis and tracking of single functional cells, and in combination with FACS to establish a high-throughput screening method for efficient, intuitive, and specific tracking of functionally active strains, can significantly improve the efficiency of isolation and selection of functional microorganisms, not only providing important technical support for single-cell level studies of functional microorganisms and the deep excavation of undiscovered functional microbial resources, but also providing valuable bacteria resources for microbial treatment and recovery of environmental pollution.

SUMMARY

One object of the present invention is, in order to overcome the above deficiencies in the prior art, to provide a core-shell type nanosilica fluorescent probe, a synthesis method thereof, and use thereof in the selection of functional microorganisms having toxic aromatic hydrocarbon degrading activity.

In order to realize the above object, the present invention provides a core-shell type nanosilica fluorescent probe, which is a nanoparticle with a core-shell structure, the core-shell structure comprising a core fluorescent dye Rod-X as shown in formula (I) and a shell dye Methyl-S as shown in formula (II), the nanoparticle NP-2 having a structure as showing in formula (III);

formula (I)

formula (II)

formula (III)

The present invention further provides a synthesis method of the core-shell type nanosilica fluorescent probe, comprising the following steps:

(1) dissolving rhodamine B and allyl bromide according to a molar ratio of 1:12 in dry DMF, adding a catalyst $Cs_2CO_3$, heating to 80° C. under nitrogen atmosphere; after reacting overnight, adding a resulting mixture to dichloromethane, washing an organic phase with saline three times, drying the organic phase with sodium sulfate anhydrous, performing vacuum distillation to remove organic solvent, and separating by passing through a silica column to obtain the core fluorescent dye Rod-X as shown in formula (I);

(2) dissolving (3-aminopropyl)triethoxysilane and methyl red according to a molar ratio of 1:1 to 1:5 in dry DMF; under nitrogen atmosphere, adding catalysts PyBOP and 4-dimethylaminopyridine, reacting in an ice bath for 1 hour, removing the ice bath, and stirring at room temperature for 24 hours; performing vacuum distillation to remove organic solvent, and separating and purifying to obtain the shell dye Methyl-S as shown in formula (II);

(3) dissolving tetraethyl orthosilicate and [3-(methacryloyloxy)propyl]trimethoxysilane according to a volume ratio of 50:1 in dry ethanol; after stirring evenly, adding catalysts ammonia and deionized water wherein a volume ratio of ammonia and deionized water is 1:1; stirring at room temperature for 12 hours, and separating by high-speed centrifugation; ultrasonically dispersing in dry ethanol, centrifuging and washing three times, and dispersing in dry ethanol to obtain surface-modified silica nanoparticles $SiO_2$-NPs;

(4) adding the core fluorescent dye as shown in formula (I) into the ethanol solution of $SiO_2$-NPs under stirring, heating to 70° C. and stirring for 1 hour under nitrogen atmosphere; adding a catalyst potassium persulfate to cause a polymerization reaction to occur, and terminating the reaction after reacting at 70° C. for 4 hours; using a high-speed centrifuge to separate out a product, washing with water and ethanol and centrifuging several times until supernatant is colorless, and thereby an intermediate NP-1 is obtained;

As a preferred embodiment of the method for the selection of functional microorganisms having toxic aromatic hydrocarbon degrading activity of the present invention, the flow cytometer is configured to operate with an excitation wavelength of 555 nm, an emission wavelength of 576 nm, and a DsRed channel.

As a preferred embodiment of the method for the selection of functional microorganisms having toxic aromatic hydrocarbon degrading activity of the present invention, when sorting with the flow cytometer, bacteria exhibiting fluorescence signal intensity of highest 5-10% is selected to be the microorganisms having toxic aromatic hydrocarbon degrading activity.

formula (III)

(5) dispersing the intermediate NP-1 in dry ethanol; under vigorous stirring, adding ammonia and deionized water according to a volume ratio of 1:5; after stirring for 45 minutes, slowly adding dropwise the ethanol solution of the shell dye Methyl-S as shown in formula (II); stirring at room temperature for 24 hours under nitrogen atmosphere; using the high-speed centrifuge to separate out a product, washing with water and ethanol and centrifuging several times until supernatant is colorless, and thereby the nanoparticle as showing in formula (III) is obtained.

The core-shell type nanosilica fluorescent probe of the present invention can be used in the selection of functional microorganisms having toxic aromatic hydrocarbon degrading activity.

Therefore, the present invention further provides a method for selection of functional microorganisms having toxic aromatic hydrocarbon degrading activity, comprising the following steps: incubating various experimental bacterial strains to logarithmic phase, collecting the bacterial strains by centrifugation, washing several times with PBS, and resuspending in PBS to a concentration of $1*10^8$ according to $OD_{600}$; mixing the various experimental bacterial strains equivalently in an inorganic salt medium, adding the nanoparticle as showing in formula (III), and incubating for 3 hours; collecting the bacterial strains by centrifugation, washing and resuspending in PBS, and sorting with a flow cytometer to obtain the microorganisms having toxic aromatic hydrocarbon degrading activity.

Compared with the prior art, the present invention has the following advantages and beneficial effects:

(1) In the present invention, a core-shell type nanosilica fluorescent probe with specific selectivity for the degradation of azo dyes has been designed and synthesized. When the azo dyes are not degraded, since fluorescence resonance energy transfer (FRET) occurs in the particles, no fluorescence will be detected; when the azo dyes have been partially degraded by the enzymes from the bacterial cells, since the structure of the azo dyes has been destroyed, fluorescence will be emitted from the fluorescence portion.

(2) In the method of the present invention for selection of functional microorganisms having toxic aromatic hydrocarbon degrading activity, where the azo dyes are used as the target compounds and azo dye-decolorizing bacterial strains are the experimental objects, it is the first time that a core-shell type nanosilica fluorescent probe is applied in the selection of functional microorganisms, and the specificity screening of functionally active bacteria is performed by adopting a coloring process of the nanoparticles, that occurs when the azo dyes are degraded in the bacterial cells, in combination with a flow cytometer. The development of this research will establish a novel research pattern for microorganism selection based on chemical fluorescent labeling technology, which enables efficient, intuitive and rapid specificity sorting and analyzing of individual cells with high sensitively, provides new tools for efficient selection of functional microorganisms, provides technical support for single-cell level studies of functional microorganisms and the deep excavation of undiscovered functional microbial resources, and has great practical significance and application potential for the prevention and control of toxic aromatic pollutants.

BRIEF DESCRIPTION OF THE DRAWINGS

FIGS. 5 to 10 show the laser confocal images of *Shewanella decolorationis* S12 incubated with the nanoprobe NP-2 of the present invention, taken at intervals during a 12-hour period. The fluorescence intensity in each visual field increases over time.

FIG. 5 shows the images taken at 0 hour.

FIG. 12 shows the fluorescent images of *Sphingobium* spp. C1 and C2 and *Escherichia coli* incubated with the nanoprobe NP-2 of the present invention for 1 hour or 12 hours, taken using a laser confocal fluorescence microscope with an excitation wavelength of 555 nm. Section A is a laser confocal image of *E. coli* incubated with the nanoprobe NP-2 for 1 hour. Section B is a laser confocal image of *E. coli* incubated with the nanoprobe NP-2 for 12 hours. Section C is a laser confocal image of the strain C1 incubated with the nanoprobe NP-2 for 1 hour. Section D is a laser confocal image of the strain C1 incubated with the nanoprobe NP-2 for 12 hours. Section E is a laser confocal image of the strain C2 incubated with the nanoprobe NP-2 for 1 hour. Section F is a laser confocal image of the strain C2 incubated with the nanoprobe NP-2 for 12 hours.

DETAILED DESCRIPTION OF THE EMBODIMENTS

In order to make the objects, technical solutions and beneficial technical effects of the present invention more clear, the present invention will be further described in detail below with reference to the embodiments. It should be understood that the embodiments described in the specification are merely illustrative of the invention but not to limit the invention. The parameters and proportions in the embodiments may be altered in accordance with the present invention without substantially affecting the results.

Embodiment 1

Figure 14:
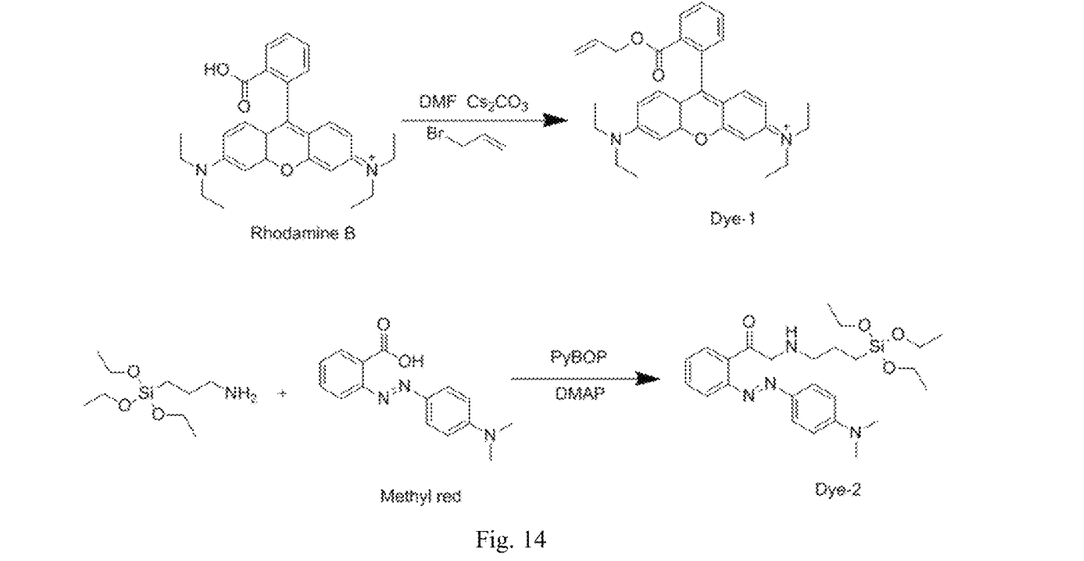
FIG. 14 shows the synthesis pathways of the dyes Rod-X and Methyl-S.
Figure 15:
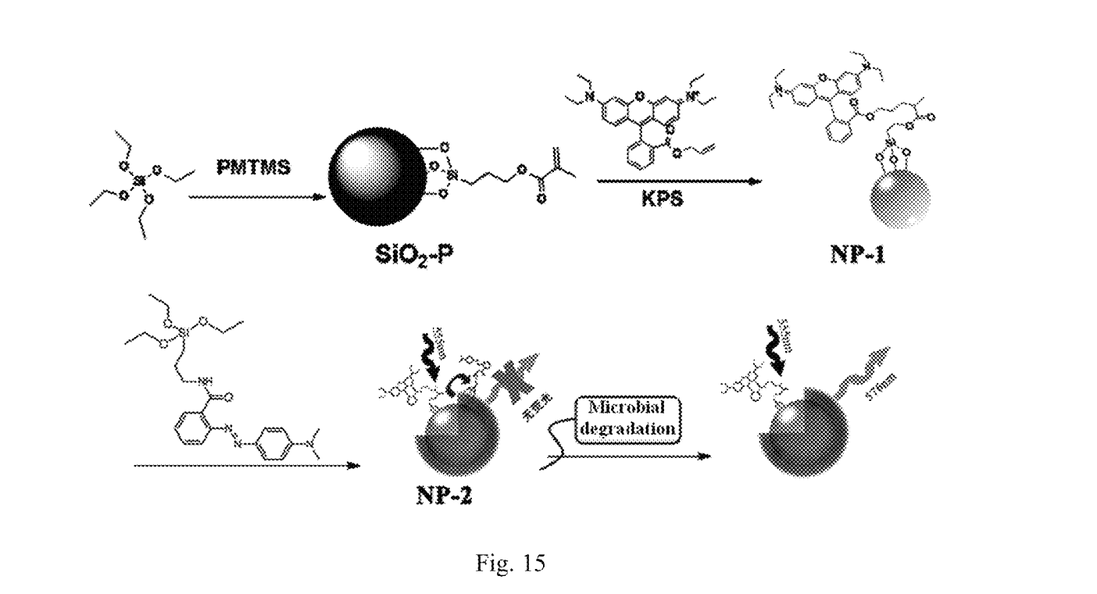
FIG. 15 is a diagram showing the synthesis of the nanoprobes NP-1 and NP-2 and the selection of functional microorganisms.

The synthesis pathways of the dyes Rod-X and Methyl-S are as shown in FIG. 14. The synthesis pathways of the nanoprobes NP-1 and NP-2 are as shown in FIG. 15. The detailed synthesis processes are as follows.

1) Synthesis of the Dye Rod-X:

0.48 g of rhodamine B, 1.46 g of allyl bromide (12 mmol), and 2.65 g of 2.65 g $Cs_2CO_3$ were added into a 100-mL volumetric flask and dissolved with 50 mL of dry DMF, heated to 80° C. under nitrogen atmosphere. After reacting overnight, the mixture was added into 200 mL of dichloromethane, the organic phase was washed with saline three times, dried using sodium sulfate anhydrous, subjected to vacuum distillation to remove organic solvent, and passed through a silica column, and thereby 0.31 g of product was obtained with a yield of 64% (methanol/dichloromethane=1:40, $R_f$=0.2). $^1$H NMR (400 MHz, $CDCl_3$) δ 1.3 (t, $CH_3$, 12H), 3.5 (q, $CH_2$, 8H), 4.5 (d, $CH_2$, 2H), 5.1 (t, $CH_2$, 2H), 5.7 (qd, CH, 1H), 6.8 (s, Ar, 2H), 6.9 (d, Ar, 2H), 7.0 (d, Ar, 2H), 7.3 (m, Ar, 1H), 7.8 (td, Ar, 2H), 8.32 (d, Ar, 1H). HRMS $C_{31}H_{35}N_2O_3$: calcd. 483.6291; found m/z 483.2642 $[M]^+$.

2) Synthesis of the Dye Methyl-S:

1 mL of (3-aminopropyl)triethoxysilane (APTES) and 1.35 g of methyl red (5 mmol) were measured out and added into a 100-mL single-neck round-bottom flask, followed by the addition of 30 mL of dehydrated DMF, and then an ice bath was employed. As the system was maintained under dry nitrogen atmosphere, 5.2 g of PyBOP (10 mmol) and 0.1 g of 4-dimethylaminopyridine (DMAP) in an effective dose were added into the round-bottom flask. After reacting for 1 hour, the ice bath was removed. The mixture was stirred under room temperature for 24 hours, subjected to vacuum distillation to remove organic solvent, and then subjected to separation and purification (ethanol/n-hexane=8:1, $R_f$=0.6). $^1$H NMR (400 MHz, DMSO) δ 1.1 (m, $CH_2$, 2H), 1.4 (t, $CH_2$, 2H), 1.7 (dd, $CH_2$, 6H), 3.0 (dd, $CH_3$, 6H), 3.4 (t, $CH_3$, 9H), 4.6 (m, NH, 1H), 6.7 (m, Ar, 1H), 7.2 (m, Ar, 1H), 7.5 (m, Ar, 2H), 7.6 (m, Ar, 2H), 7.8 (m, Ar, 1H), 8.0 (m, Ar, 1H). FIRMS $C_{25}H_{38}N_4O_4$: calcd. 486.6851; found m/z 486.2525 $[M]^+$.

3) Synthesis of the Fluorescent Nanoparticles NP-1:

5 mL of pure tetraethyl orthosilicate and 0.1 mL of [3-(methacryloyloxy)propyl]trimethoxysilane (PMTMS)

were dissolved in 50 mL of dry ethanol. After stirring evenly, 1 mL of deionized water and 1 mL of ammonia were added. The mixture was stirred at room temperature for 12 hours, and then the resulting nanoparticles were separated out using a high-speed centrifuge. The nanoparticles were then dispersed in ethanol and centrifuged three times to give the modified nanosilica product. The product was dispersed in dry ethanol, and then the fluorescent dye Rod-X was added into the solution for polymerization; the solution was heated to 70° C. and stirred for 1 hour under nitrogen atmosphere, and then 15 mg of KPA was added to initiate the polymerization reaction. After reacting at 70° C. for 4 hours, the reaction was terminated, and then the product NP-1 was separated out using the high-speed centrifuge.

4) Synthesis of the Fluorescent Nanoparticles NP-2:

The obtained nanoparticles NP-1 were dispersed in dry ethanol, and then 0.2 mL of concentrated ammonia and 1 mL of deionized water were added under vigorous stirring; after stirring for 1 hour, the ethanol solution of Methyl-S was slowly added dropwise into the reaction solution which was then stirred at room temperature for 24 hours under nitrogen atmosphere, the resulting product was separated out using the high-speed centrifuge.

Figure 1:
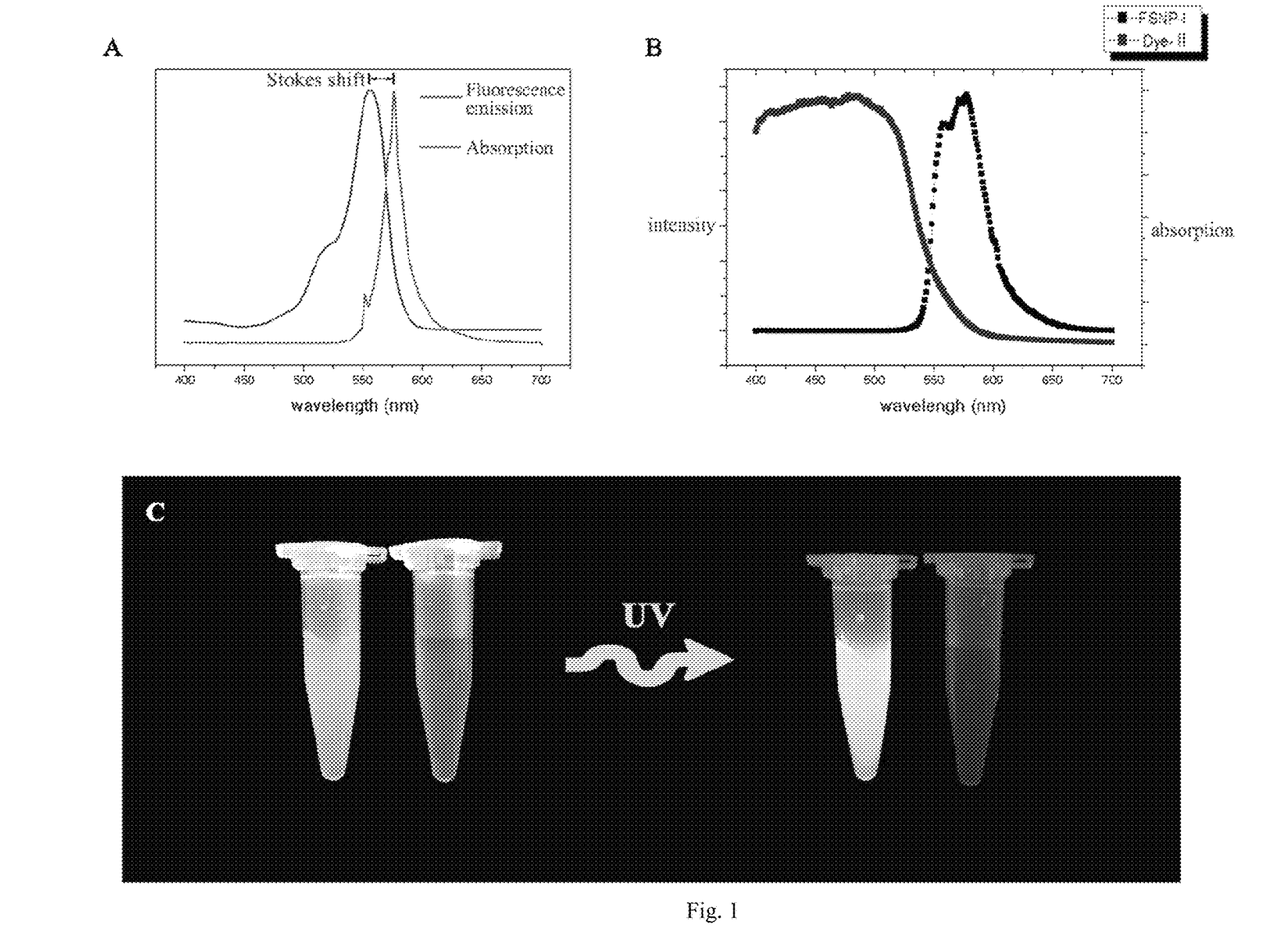
FIG. 1 shows the spectroscopic analysis of the nanoprobes. Section A shows an absorption spectrum and a fluorescence emission spectrum of the dye Rod-X. Section B shows an absorption spectrum of the dye Methyl-S and a fluorescence emission spectrum of the NP-1. Section C shows the appearances of NP-1 and NP-2 under the irradiation of natural light and a handheld ultraviolet lamp; under natural light, NP-1 is pink and NP-2 is brownish yellow; under ultraviolet light, NP-1 emits bright orange-yellow fluorescence, while NP-2 does not emit fluorescence.

The nanoparticles NP-2 has a structure as shown in formula (III):

FIG. 1 shows the spectroscopic analysis of the nanoprobes and dyes. Section A shows an absorption spectrum and a fluorescence emission spectrum of the dye Rod-X, wherein the maximum absorption wavelength is 555 nm, the maximum emission wavelength is 576 nm, and the Stokes shift is 21 nm. Section B shows an absorption spectrum of the dye Methyl-S and a fluorescence emission spectrum of the NP-1, wherein an overlap between the fluorescence emission spectrum and the absorption spectrum is observed, indicating that the dye Methyl-S and NP-1 can be combined to form a core-shell type nanoparticle that meets the requirements according to the FRET principle. Section C shows the appearances of NP-1 and NP-2 under the irradiation of natural light and a handheld ultraviolet lamp; under natural light, NP-1 is pink and NP-2 is brownish yellow; under ultraviolet light, NP-1 emits bright orange-yellow fluorescence, while NP-2 does not emit fluorescence.

Embodiment 3

Morphology of the Nanoparticles:

The nanoparticles of different stages were dried at 60° C. over night in a vacuum oven. After being fully dried, they were ground powders and subjected to thermogravimetric analysis which was carried out under nitrogen atmosphere formula (III)

Embodiment 2

Figure 3:
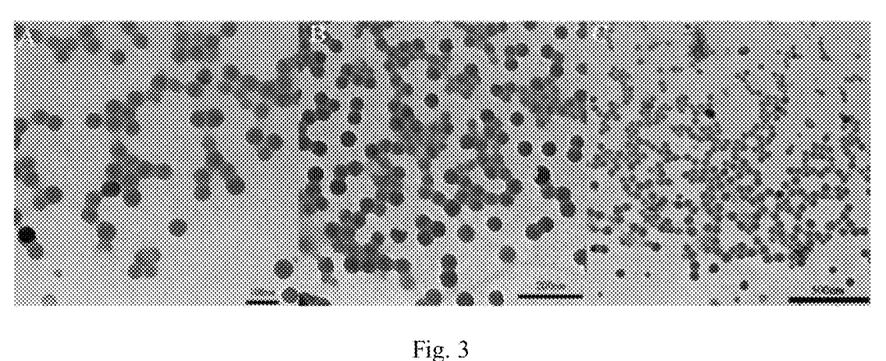
FIG. 3 shows the TEM images of the nanoprobe NP-2 of the present invention taken at different magnifications, wherein, section A is an image with a magnification of 20000 and the scale bar therein indicates a length of 100 nm, section B is also an image with a magnification of 20000 and the scale bar therein indicates a length of 200 nm, and section C is an image with a magnification of 10000 and the scale bar therein indicates a length of 500 nm.
Figure 4:
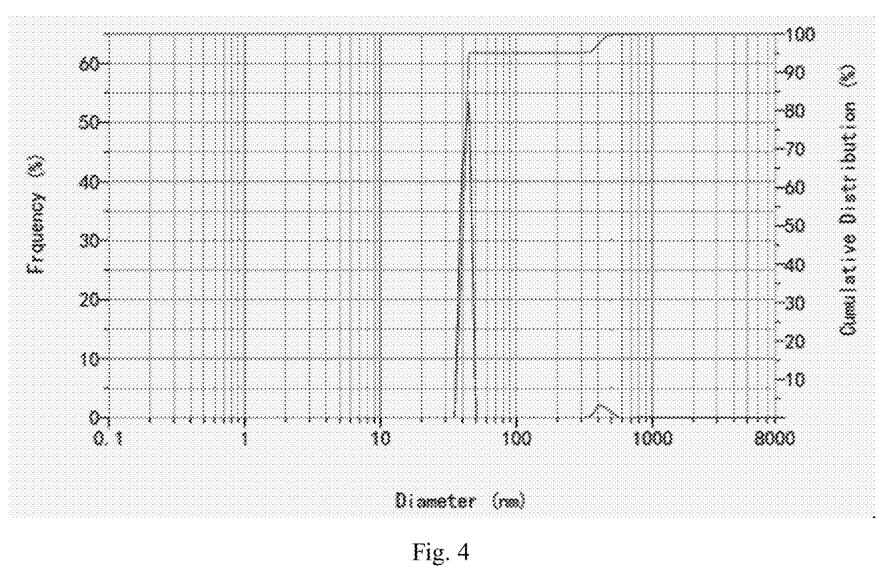
FIG. 4 shows the particle size distribution results of the nanoprobe NP-2 of the present invention based on the dynamic light scattering test, indicating an average particle size of 59.0 nm.
Figure 5:
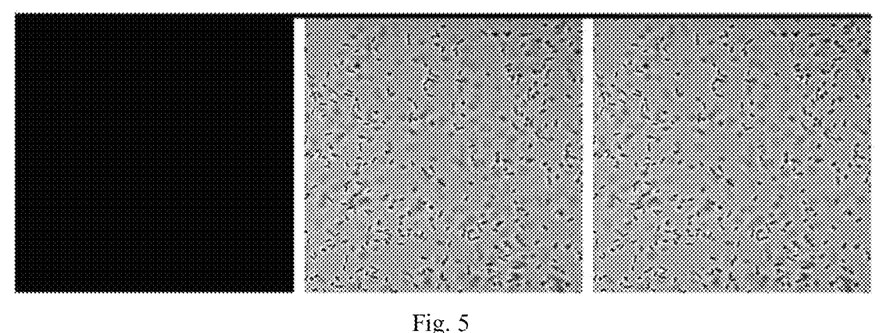
Figure 6:
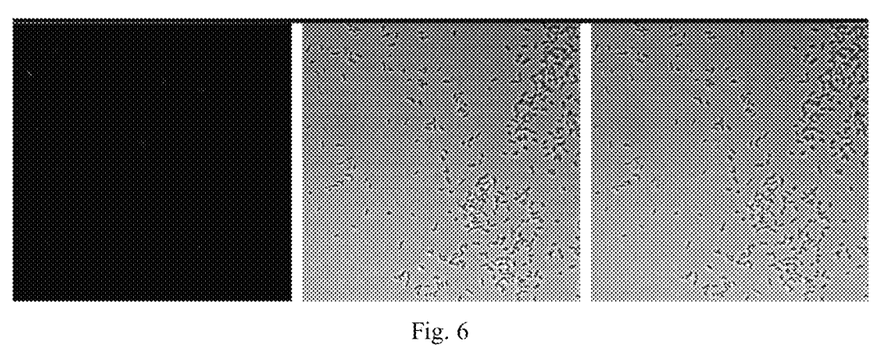
FIG. 6 shows the images taken after 1 hour.
Figure 7:
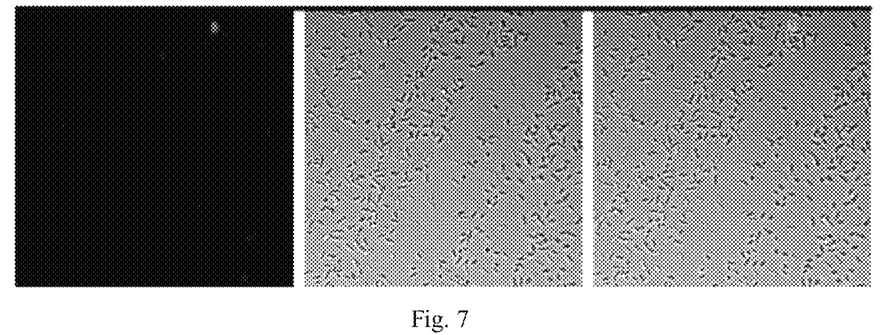
FIG. 7 shows the images taken after 2 hours.
Figure 8:
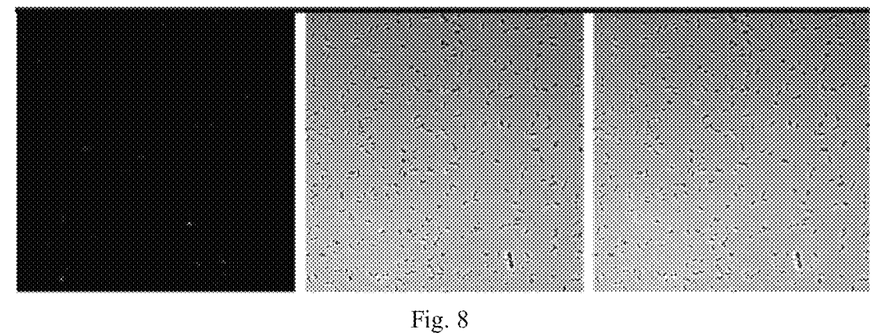
FIG. 8 shows the images taken after 3 hours.
Figure 9:
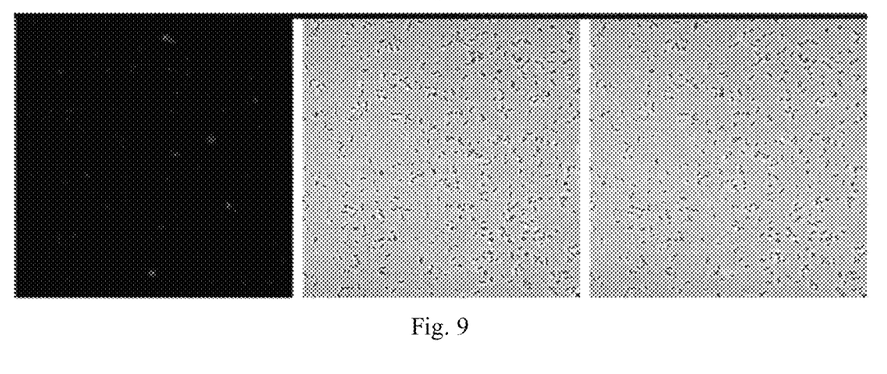
FIG. 9 shows the images taken after 6 hours.
Figure 10:
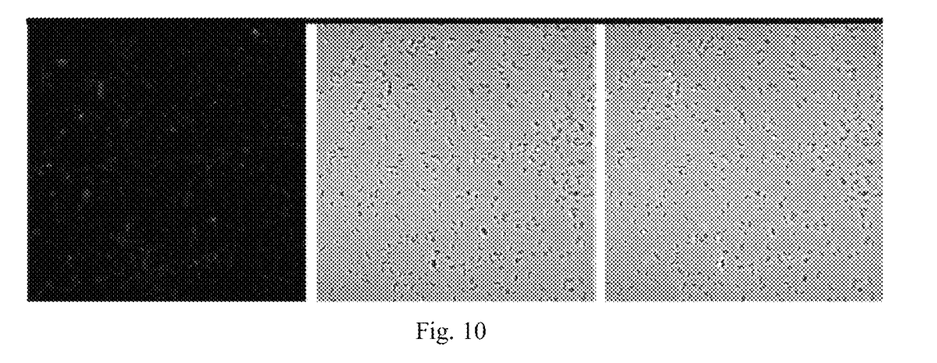
FIG. 10 shows the images taken after 12 hours.

Spectrum of the Nanoprobes:

The dye Rod-X and the dye Methyl-S were dissolved in ethanol, the nanoparticles were dispersed in an aqueous solution, and thereby their infrared spectra, absorption spectra and fluorescence spectra were measured. The infrared spectrum measurement was carried out using a FTIR spectrometer (Bruker/Tensor II) over a range from 4000 cm$^{-1}$ to 400 cm$^{-1}$. The ultraviolet spectrum measurement was carried out using a UV-Vis spectrophotometer (SHIMADZU/UV-2600) over a range from 400 nm to 800 nm. The fluorescence spectra measurement was carried out using a spectrofluorometer (Perkin Elmer/LS-45) over an excitation wavelength range from 200 nm to 600 nm and an emission wavelength range from 400 nm to 800 nm. Observation on the emission of the nanoparticles was carried out with a handheld UV lamp.

over a temperature range from 30° C. to 700° C. with a heating rate of 10° C./min. The fluorescent nanoprobes were dispersed in an aqueous solution, and thereby the forms and sizes of the particles were determined using a transmission electron microscope (TEM), and the particle size distributions were measured by carrying out dynamic light scattering (DLS) (FIGS. 2 to 4).

Figure 2:
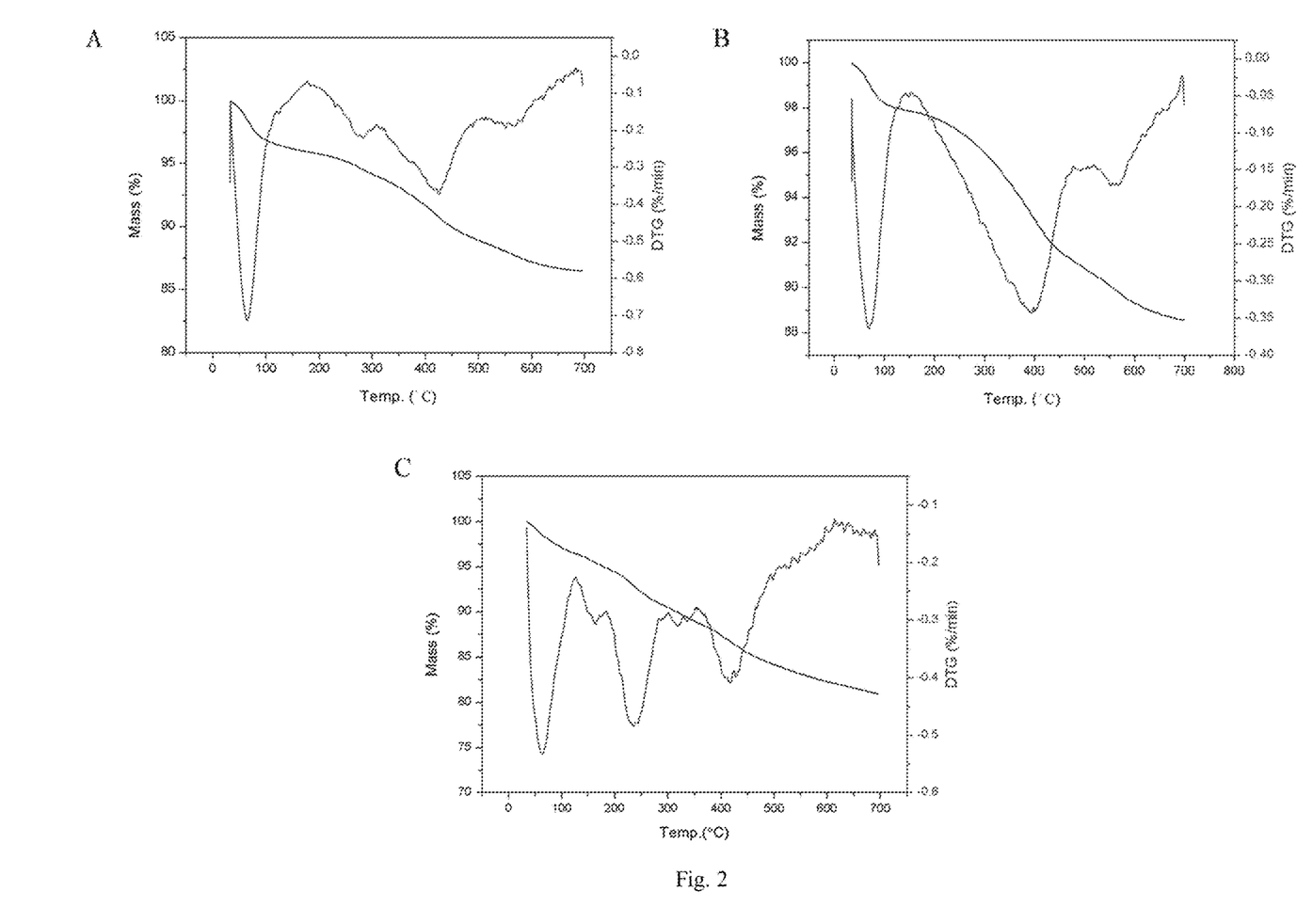
FIG. 2 shows the thermogravimetric analysis results of the nanoparticles in various stages. Section A shows the thermogravimetric analysis result of the silica nanoparticles not bound with the dyes. Section B shows the thermogravimetric analysis result of NP-1. Section C shows the thermogravimetric analysis result of NP-2.

FIG. 2 shows the thermogravimetric analysis results of the nanoparticles of the present invention in various stages. Section A is the TGA graph of the silica nanoparticles not bound with the dyes, exhibiting two mass losses that they lost about 9% of the mass. Section B is the TGA graph of NP-1, exhibiting two mass losses that they lost about 10% of the mass. Section C is the TGA graph of NP-2, exhibiting three mass losses that they lost about 12% of the mass. FIG. 3 shows the TEM images of the nanoprobe taken at different magnifications, revealing that the nanoparticles were well dispersed and had a regular spherical shape with an average particle size of 50±10 nm. FIG. 4 shows the particle size distribution of the nanoprobe NP-2 based on the dynamic light scattering test, indicating an average particle size of 59.0 nm.

Embodiment 4

Tracing of Bacteria Using the Fluorescent Nanoprobe:

Shewanella decolorationis S12 (a prior art bacterial strain, disclosed in: Xu, Meiying; Guo, Jun; Zeng, Guoqu; Zhong, Xiaoyan; Sun, Guoping. Decolorization of anthraquinone dye by Shewanella decolorationis S12. Applied Microbiology and Biotechnology, 2006, 71: 246-251), Sphingobium sp. C1, Sphingobium sp. C2, and Escherichia coli, were inoculated to an Erlenmeyer flask containing 40 mL of Luria-Bertani medium (LB medium, 10 g/L of tryptone, 5 g/L of yeast extract, 10 g/L of NaCl, pH=7.4), and incubated on a shaker overnight to ensure complete growth. 10 μL of the preincubated bacterial solution was transferred to an Erlenmeyer flask containing 4 mL of fresh LB medium, incubated on the shaker for 8 hours, and subjected to centrifugation (7500 rmp, 10 min, 25° C.). The collected bacteria were washed with PBS (phosphate buffer saline, 137 mM of NaCl, 2.7 mM of KCl, 10 mM of $Na_2HPO_4$, 2 mM of $KH_2PO_4$, pH=7.4) three times, and then resuspended in PBS to give a bacterial suspension with an $OD_{600}$ value of 0.1. 3 mL of the bacterial suspension was added with 30 μL of chloromycetin (0, 2.5 μg/mL) and 40 μL of NP-2 (100 μg/mL, PBS), and after incubated for 1 hour, 2 hours, 3 hours, 6 hours or 12 hours, centrifuged and washed with PBS for three times. The residue was then resuspended in PBS to give a bacterial suspension.

Figure 11:
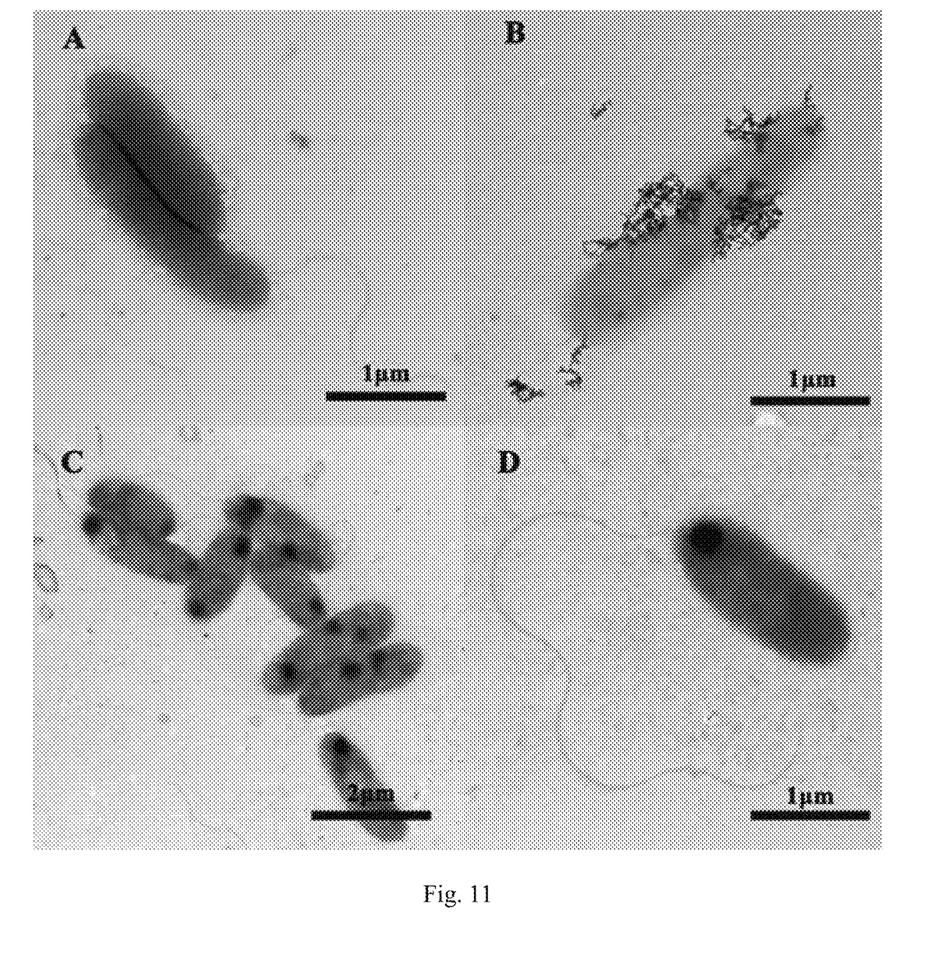
FIG. 11 shows the TEM images of *Shewanella decolorationis* S12 incubated with the nanoprobe NP-2 of the present invention for 12 hours. Section A is an image of the bacterial strain incubated without the addition of chloromycetin. Sections B, C and D are images of the bacterial strain incubated with the addition of chloromycetin, wherein section B reveals the nanoparticles entering the bacterial cell, while sections C and D reveals the accumulation of the nanoparticles in the cells.
Figure 12:
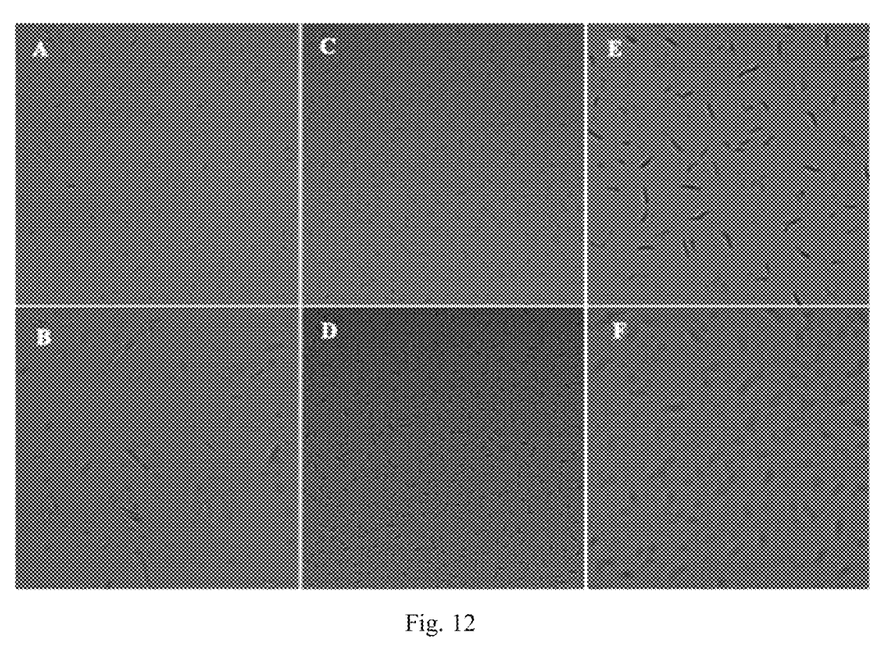
Figure 13:
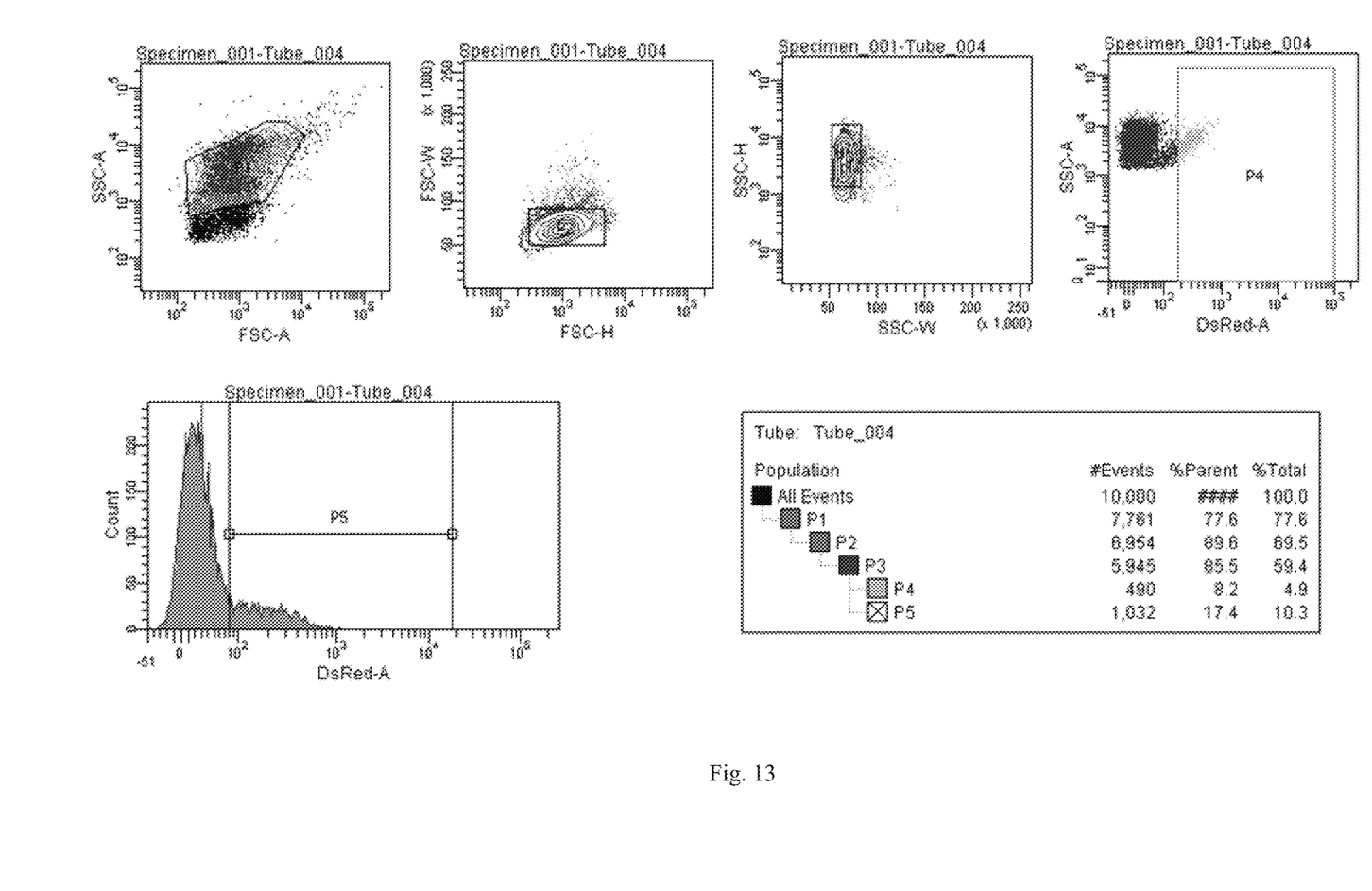
FIG. 13 shows the graphs of a flow sorting experiment. The flow sorting was performed using a BD FACSAria III flow cytometer with an excitation wavelength of 555 nm. The bacteria exhibiting the highest relative fluorescence intensity was selected, constituting 10.3% of the total population.

FIGS. 5 to 10 show the laser confocal images of Shewanella decolorationis S12 after incubated with NP-2 for 0 hour, 1 hour, 2 hours, 3 hours, 6 hours and 12 hours. As the incubation time increased, the fluorescence intensity in each visual field increased, indicating that as the incubation time increased, more and more azo dyes on NP-2 were reduced by the S12 strain and thereby emitted fluorescent signals. After incubated for 3 hours, there were significantly more fluorescent signals observed, and the fluorescence intensity was significantly increased. FIG. 11 shows the TEM images of Shewanella decolorationis S12 incubated with NP-2. Section A shows the bacterial strain incubated without the addition of chloromycetin. Sections B, C and D shows the bacterial strain incubated with the addition of chloromycetin. As can be seen from the images, the presence of chloromycetin could promote the nanoparticles to enter the cells and accumulate in the cells which led to the obvious fluorescence radiance in the cells. In FIG. 12, sections A and B shows the laser confocal images of E. Coli incubated with NP-2 for 1 hour and 12 hours, sections C and D shows the laser confocal images of the Sphingobium sp. C1 incubated with NP-2 for 1 hour and 12 hours, and sections E and F shows the laser confocal images of the Sphingobium sp. C2 incubated with NP-2 for 1 hour and 12 hours. As can be seen from the images, since these bacterial species did not have azo dye degrading function, the azo dyes on NP-2 had not been degraded, and thereby barely no fluorescent signal was observed under laser confocal microscopy even after a 12-hour incubation.

Embodiment 5

Flow Sorting of the Microorganism Having Degrading Function:

The prepared nano particles were applied to a complex bacterial population, and a flow cytometer was used to perform functional specificity analysis and sorting. Shewanella decolorationis S12, which was known to have azo dye decolorizing function, and Sphingobium sp. C1, Sphingobium sp. C2, and Escherichia coli, which had no decolorizing function, were respectively incubated to logarithmic phase, followed by the addition of the nanoparticles and chloromycetin. They were further incubated for 3 hours and then mixed equivalently. Sorting was then performed with the flow cytometer to sort out single fluorescent bacteria, which were then verified by a decolorization process and identified by 16S rDNA sequencing.

The complex bacterial population employed in the flow sorting trial comprised Shewanella decolorationis S12, Sphingobium sp. C1, Sphingobium sp. C2, and Escherichia coli, wherein only Shewanella decolorationis S12 exhibited decolorization-fluorescence function on NP-2 while the other species did not have this function. Thus, the single bacteria sorted out from the complex must be the strain S12. The flow sorting was performed using a BD FACSAria III flow cytometer with an excitation wavelength of 555 nm. The bacteria exhibiting the highest relative fluorescence intensity was selected, constituting 10.3% of the total population (FIG. 12). According to the 16S rDNA sequencing data, the bacteria sorted out only included the strain S12.

The above embodiments may be amended or modified by those skilled in the art in light of the disclosure and teaching of the specification. Therefore, the invention is not limited to the specific embodiments disclosed and described herein, and the amendments and modifications to the invention are intended to fall within the scope of the appended claims. In addition, although specific terms are used in the specification, these terms are merely for convenience of description and do not limit the invention.

What is claimed is:

1. A core-shell type nanosilica fluorescent probe, wherein the core-shell type nanosilica fluorescent probe is a nanoparticle with a core-shell structure, the core-shell structure comprises a core fluorescent dye having a chemical structure of formula (I) and a shell dye having a chemical structure of formula (II), and the nanoparticle has a structure of formula (III);

formula (I)

formula (II)

-continued formula (III)

2. A synthesis method of the core-shell type nanosilica fluorescent probe of claim 1, comprising the following steps:
(1) dissolving rhodamine B and allyl bromide according to a molar ratio of 1:12 in dry dimethylformamide (DMF), adding $Cs_2CO_3$, and heating to 80° C. under nitrogen atmosphere; after reacting overnight to obtain a first mixture, adding the first mixture to dichloromethane to obtain an organic phase, washing the organic phase with saline three times, drying the organic phase with sodium sulfate anhydrous, performing vacuum distillation on the organic phase to remove organic solvent to obtain a second mixture, and separating the second mixture by passing through a silica column to obtain the core fluorescent dye of the formula (I);
(2) dissolving (3-aminopropyl)triethoxysilane and methyl red according to a molar ratio of 1:1 to 1:5 in dry DMF to obtain a first solution; under nitrogen atmosphere, adding PyBOP and 4-dimethylaminopyridine to the first solution, reacting the first solution in an ice bath for 1 hour, removing the ice bath, and stirring the first solution at room temperature for 24 hours; performing vacuum distillation on the first solution to remove organic solvent to obtain a third mixture, and separating and purifying to obtain the shell dye of the formula (II);
(3) dissolving tetraethyl orthosilicate and [3-(methacryloyloxy)propyl]trimethoxysilane according to a volume ratio of 50:1 in dry ethanol to obtain a second solution; adding ammonia and deionized water into the second solution to obtain a third solution, wherein a volume ratio of the ammonia and the deionized water is 1:1; stirring the third solution at room temperature for 12 hours, and separating the third solution by centrifugation to obtain a supernatant and a precipitate; removing the supernatant, ultrasonically dispersing the precipitate in dry ethanol, centrifuging and washing the precipitate three times, and dispersing the precipitate in dry ethanol to obtain an ethanol solution of $SiO_2$-NPs;
(4) adding the core fluorescent dye of the formula (I) into the ethanol solution of $SiO_2$-NPs under stirring to obtain a fourth solution, heating the fourth solution to 70° C. and stirring the fourth solution for 1 hour under nitrogen atmosphere; adding potassium persulfate into the fourth solution to cause a polymerization reaction to occur, and terminating the polymerization reaction after reacting at 70° C. for 4 hours; using a centrifuge to separate out a first product from the fourth solution, washing the first product with water and ethanol to obtain a fifth solution and centrifuging the fifth solution a plurality of times until a supernatant of the fifth solution is colorless to obtain an intermediate NP-1;
(5) dispersing the intermediate NP-1 in dry ethanol to obtain a sixth solution; under stirring, adding ammonia and deionized water according to a volume ratio of 1:5 into the sixth solution to obtain a seventh solution; after stirring the seventh solution for 45 minutes, adding dropwise an ethanol solution of the shell dye of the formula (II) into the seventh solution to obtain an eighth solution; stirring the eighth solution at room temperature for 24 hours under nitrogen atmosphere; using the centrifuge to separate out a second product from the eighth solution, washing the second product with water and ethanol to obtain a ninth solution and centrifuging the ninth solution a plurality of times until a supernatant of the ninth solution is colorless to obtain the nanoparticle of the formula (III).

3. A selection method for functional microorganisms having toxic aromatic hydrocarbon degrading activity, comprising the following steps:
incubating different types of experimental bacterial strains to logarithmic phase, respectively, collecting the bacterial strains by centrifugation, washing a plurality of times with phosphate-buffered saline (PBS), and resuspending in PBS to a concentration of $1\times10^8$ according to $OD_{600}$; mixing the experimental bacterial strains equivalently in an inorganic salt medium to obtain a first mixed bacterial strain solution, adding nanoparticles of formula (III) into the first mixed bacterial strain solution, and incubating the first mixed bacterial strain solution for 3 hours; collecting bacterial strains from the mixed bacterial strain solution by centrifugation, washing and resuspending the bacterial strains in PBS to obtain a second mixed bacterial strain solution, and sorting with a flow cytometer to obtain the microorganisms having toxic aromatic hydrocarbon degrading activity:

formula (III)

-continued

4. The selection method for the functional microorganisms having toxic aromatic hydrocarbon degrading activity according to claim 3, wherein, the flow cytometer is configured to operate with an excitation wavelength of 555 nm, an emission wavelength of 576 nm, and a DsRed channel.

5. The selection method for the functional microorganisms having toxic aromatic hydrocarbon degrading activity according to claim 3, wherein, when sorting with the flow cytometer, bacteria exhibiting fluorescence signal intensity of highest 5%-10% are selected to be the microorganisms having toxic aromatic hydrocarbon degrading activity.

* * * * *

UNITED STATES PATENT AND TRADEMARK OFFICE
CERTIFICATE OF CORRECTION

PATENT NO. : 10,732,109 B2  
APPLICATION NO. : 16/492161  
DATED : August 4, 2020  
INVENTOR(S) : Meiying Xu et al.

Page 1 of 1

It is certified that error appears in the above-identified patent and that said Letters Patent is hereby corrected as shown below:

On the Title Page

Item (73) Assignee should read: GUANGDONG INSTITUTE OF MICROBIOLOGY (GUANGDONG DETECTION CENTER OF MICROBIOLOGY), Guangzhou, (CN); GUANGDONG ACADEMY OF SCIENCES, Guangzhou, (CN)

Signed and Sealed this  
Sixteenth Day of February, 2021

Drew Hirshfeld  
*Performing the Functions and Duties of the*  
*Under Secretary of Commerce for Intellectual Property and*  
*Director of the United States Patent and Trademark Office*